(12) United States Patent
Grases Freixedas et al.

(10) Patent No.: US 10,149,851 B2
(45) Date of Patent: Dec. 11, 2018

(54) THEOBROMINE OR ITS DERIVATIVES FOR THE TREATMENT OR PREVENTION OF RENAL LITHIASIS

(71) Applicant: UNIVERSITAT DE LES ILLES BALEARS, Palma de Mallorca (Islas Baleares) (ES)

(72) Inventors: Félix Grases Freixedas, Palma de Mallorca (ES); Antonia Costa Bauzá, Palma de Mallorca (ES); Rafael María Prieto Almirall, Palma de Mallorca (ES); Adrián Rodríguez Rodríguez, Palma de Mallorca (ES)

(73) Assignee: UNIVERSITAT DE LES ILLES BALEARS, Palma de Mallorca (Islas Baleares) (ES)

( * ) Notice: Subject to any disclaimer, the term of this patent is extended or adjusted under 35 U.S.C. 154(b) by 0 days.

(21) Appl. No.: 15/313,269

(22) PCT Filed: Apr. 15, 2015

(86) PCT No.: PCT/ES2015/070301
§ 371 (c)(1),
(2) Date: Nov. 22, 2016

(87) PCT Pub. No.: WO2015/181412
PCT Pub. Date: Dec. 3, 2015

(65) Prior Publication Data
US 2017/0143724 A1 May 25, 2017

(30) Foreign Application Priority Data

May 29, 2014 (ES) .................................. 201430819

(51) Int. Cl.
*A23L 33/10* (2016.01)
*A61K 31/522* (2006.01)

(52) U.S. Cl.
CPC ............ *A61K 31/522* (2013.01); *A23L 33/10* (2016.08); *A23V 2002/00* (2013.01)

(58) Field of Classification Search
CPC .... A23L 33/10; A23V 2002/00; A61K 31/522
See application file for complete search history.

(56) References Cited

U.S. PATENT DOCUMENTS

| | | | | |
|---|---|---|---|---|
| 3,624,205 | A * | 11/1971 | Hitchings | A61K 31/505 514/262.1 |
| 6,348,470 | B1 * | 2/2002 | Korbonits | A61K 31/522 424/450 |
| 2012/0065236 | A1 * | 3/2012 | Gunawardhana | A61K 31/415 514/365 |

FOREIGN PATENT DOCUMENTS

WO WO 95/15164 A1 6/1995
WO WO 2011/144545 A1 11/2011

OTHER PUBLICATIONS

Kela (Life Sciences, 27, 2109-2119, 1980).*
Bouropoulos et al. (J of Endourology, 24, Sep. 2010, Abstract PS3-19).*
Grases et al. (Nutrition Journal, 5, 23, 2006, p. 1-7).*
International Preliminary Report on Patentability in corresponding PCT Application No. PCT/ES2015/070301, dated Nov. 29, 2016.
International Search Report and Written Opinion in corresponding PCT Application No. PCT/ES2015/070301, dated Jul. 22, 2015.
Bouropoulos C Et Al: "The Effect of Theophylline on in Vitro Calcium Oxalate Formation", Journal of Endourology, vol. 1. 24, No. Suppl 1, Sep. 1, 2010 (Sep. 1, 2010), page A21.
Shekarri Z et al: "Uric Acid Nephrolithiasis: Current Concepts and Controversies", Journal of Urology, Lippincott Williams & Wilkins, vol. 168, No. 4, Oct. 1, 2002 (Oct. 1, 2002), pp. 1307-131.
Grases Felix et al: "Thobromine inhibits uric acid crystallization. A potential application in the treatment of uric acid nephrolithiasis.", PLOS ONE 2014, vol. 9, No. 10, E111184, 2014, pp. 1.
Grases F et al., Uric Acid Urolithiasis and Crystallization Inhibitors, Urol. Int. 1999; 62(4): pp. 201-204.
Ngo TC, el al., Uric Acid Nephrolithiasis: Recent Progress and Future Directions Rev. Urol. 2007; 9(1): pp. 17-27.

* cited by examiner

*Primary Examiner* — Umamaheswari Ramachandran
(74) *Attorney, Agent, or Firm* — Leason Ellis LLP

(57) ABSTRACT

The present invention refers to the use of theobromine or its derivatives as an inhibitor of the crystallization of uric acid to avoid the formation of uric acid crystals in urine and as a consequence renal lithiasis or specifically uric acid renal lithiasis.

5 Claims, 4 Drawing Sheets

THEOBROMINE OR ITS DERIVATIVES FOR THE TREATMENT OR PREVENTION OF RENAL LITHIASIS

CROSS-REFERENCE TO RELATED PATENT APPLICATIONS

This application is a U.S. National Phase Application under 35 U.S.C. § 371 of International Patent Application No. PCT/ES2015/070301, filed Apr. 15, 2015, and claims the priority of Spanish Application No. P201430819, filed May 29, 2014. The International Application was published on Dec. 3, 2015 as International Publication No. WO2015/181412 A1.

The present invention refers to the use of theobromine or its derivatives as an inhibitor of uric acid crystallisation to avoid the formation of uric acid crystals in urine and as a consequence uric acid renal lithiasis.

STATE OF THE ART

It is current knowledge that the fundamental problem of uric acid renal lithiasis lies in the more or less persistent existence of urinary pH values below 5.5. Urinary supersaturation with uric acid linked to the excretion of this substance is important but there are almost no cases where it has been demonstrated to be a decisive factor in the development of urolithiasis. Intuitively, it seems likely that the presence of uric acid crystallisation inhibitors must be relevant, since in individuals with the same urinary pH values and concentrations of uric acid some form uric acid renal calculi and others do not. However, although some in vitro studies of potential uric acid crystallisation inhibitors have been performed, which have shown that saponins, glycosaminoglycans and glycoproteins exhibit a remarkable ability to inhibit the crystallisation of uric acid, there is no known clinical study on this subject.

Currently, the prophylactic treatment of uric acid renal lithiasis is based on the implementation of dietary measures to reduce uric acid levels in the urine and in turn increase urinary pH levels. This is why it is recommended to reduce the excessive consumption of animal protein (red meat, seafood, oily fish, offal, etc.) and alcoholic drinks and to increase the consumption of fruit (mainly citrus) and vegetables, as well as carbonated drinks. The only pharmaceutical drugs currently used to treat uric acid renal lithiasis are citrate as a urinary basifying agent and, in those cases where hyperuricemia is detected, the synthesis of uric acid in the plasma is reduced through oral administration of allopurinol or febuxostat in order to inhibit the xanthine oxidase enzyme, which is responsible for the synthesis of uric acid (Grases F et al., Urol. Int. 1999; 62(4):201-4; Ngo T C, el al. Rev. Urol. 2007; 9(1):17-27).

Therefore, the therapeutic arsenal available for the treatment of uric acid renal lithiasis is still very limited, prompting interest in new therapeutic strategies that provide new solutions to this pathology.

DESCRIPTION OF THE INVENTION

The objective of the new invention is to present a new product for the treatment of uric acid renal lithiasis based on the discovery of a new and potent uric acid crystallisation inhibitor. This product will be a xanthine derivative, with the 3 and 7 positions modified by a linear or branched chain containing alkyl groups of one to six carbon atoms; the chains may be identical or different from each other—for example, with the $R_1$ and $R_2$ groups as methyl groups, a dimethylxanthine called theobromine.

Theobromine ($C_7H_8N_4O_2$, chemical name 3,7-dimethylxanthine or 3,7-dihydro-3,7-dimethyl-1H-purine-2,6-dione) is an alkaloid from the methylxanthine family, a family that also includes theophylline and caffeine. Theobromine has two methyl groups in comparison with the three groups that caffeine contains.

Therefore, a primary aspect of the present invention relates to the use of a compound with the general formula (I):

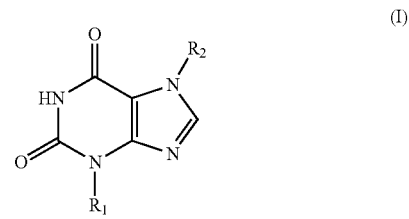

where: $R_1$ and $R_2$ are identical or different and represent an alkyl group ($C_1$-$C_6$) or any of their pharmaceutically acceptable salts for the production of a composition for the treatment and/or prevention of renal lithiasis, preferably uric acid renal lithiasis.

The term "alkyl" in the present invention refers to linear or branched saturated hydrocarbon chains that have 1 to 6 carbon atoms, for example, methyl, ethyl, n-propyl, i-propyl, n-butyl, tert-butyl, sec-butyl, n-pentyl, n-hexyl, etc., more preferably of 1 to 3 carbon atoms and more preferably it is a methyl.

In a preferred embodiment, $R_1$ is an alkyl group ($C_1$-$C_3$), more preferably $R_1$ is a methyl.

In another preferred embodiment, $R_2$ is an alkyl group ($C_1$-$C_3$), more preferably $R_2$ is a methyl.

In a more preferred embodiment, $R_1$ and $R_2$ are both a methyl group.

Given that it has been demonstrated with the present invention that compounds with general formula (I) are uric acid crystallisation inhibitors, in another preferred embodiment, the compound with formula (I), as previously described, is used to produce a composition intended to reduce risks and improve the health status of patients with diseases related to the crystallisation of uric acid, such as, for example, uric acid renal lithiasis.

Theobromine is found in fairly high concentrations in chocolate. A 50 g piece of black or bitter chocolate, which contains a minimum of 34% up to a maximum of 98% cocoa, may contain an average of 378 mg theobromine. This amount of chocolate is obviously safe and can be eaten without any type of side effects. A dose of over 1000 mg has been safely used in clinical trials without secondary or toxic effects, although it can cause mild stomach upset. A great amount of cocoa must be eaten for theobromine to have any harmful effects on humans. Although theobromine does not cause harmful effects in humans it is highly toxic to some domestic animals, including dogs and cats. A low dose of theobromine in animals can cause cardiac arrhythmias, convulsions and even death.

Therefore, in a preferred embodiment the present invention refers to the use of a preparation of a compound with formula (I), more preferably of theobromine, for its use in a composition (pharmaceutical or nutraceutical composition, functional food or dietary supplement) for the treatment or prevention of renal lithiasis, preferably uric acid renal lithiasis. The dose used varies between 100 mg/day up to 380 mg/day.

The terms "renal lithiasis", "urolithiasis" or "nephrolithiasis" refer to the disorder caused by the presence of calculi or stones inside the kidneys or the urinary tract (ureters, bladder). Renal calculi are composed of substances normally found in urine (calcium salts, uric acid, cysteine, etc.) that for different reasons have become concentrated and precipitated out forming fragments of varying size.

The term "uric acid crystals" or "uric acid calculi" includes all those processes or conditions that involve/induce the formation of precipitated solids in the urine that this substance is involved in.

In a preferred embodiment, the composition is a pharmaceutical or nutraceutical composition or functional food.

In the present invention, a "nutraceutical composition" or "functional food" is understood as a food that has a beneficial effect on health. Similarly, the term "nutraceutical" can be applied to extracts or chemical compounds obtained from common foods. Examples of foods that have been attributed with nutraceutical properties are olive oil, red wine, broccoli, soybeans, etc. Nutraceuticals are normally used in nutritional mixtures and in the pharmaceutical industry. Just as some foods can be classified as nutraceuticals it is also possible to classify some nutritional supplements in the same way, such as, for example, fatty acids such as omega-3 derived from fish oil and from some vegetables or antioxidants and vitamins.

The compound with formula (I), and particularly theobromine, can be administered in solid form (including granules, powder or suppositories) or in liquid form (such as solutions, suspensions or emulsions). It can be administered in this way or even after being subjected to operations such as sterilisation or the addition of preservatives, stabilisers or emulsifiers.

The administration of the compound with formula (I), and particularly theobromine, can be combined with one or more compounds that facilitate its absorption through a selected administration route. It can, therefore, be administered with lactose, sucrose, talc, magnesium stearate, cellulose, calcium salts, gelatine, fatty acids, as well as other similar substances.

The pharmaceutically acceptable adjuvants and vehicles that can be used in said compositions are the adjuvants and vehicles known to experts in the field and are commonly used in preparing therapeutic compositions.

For therapeutic use, it is preferable if the compound with formula (I), particularly theobromine, is in a pharmaceutically acceptable form or is substantially pure, that is, that it has a pharmaceutically acceptable level of purity excluding the normal pharmaceutical additives, such as diluents and carriers, and is free from any materials considered toxic at normal dosage levels. The purity levels for the active substance are preferably above 50%, more preferably above 70%, and still more preferably above 90%. In a preferred embodiment, the levels of the compound with formula (I), or its salts or solvates, are above 95%.

Throughout the description and the claims, the word "comprise" and its variations are not intended to exclude other technical characteristics, additives, components or steps. For the experts in the field, other objects, advantages and characteristics of the invention will arise partly from the description and partly from practice with the invention. The following examples and figures are provided by way of illustration and are not intended to be limiting of the present invention.

EXAMPLES

Figure 1:
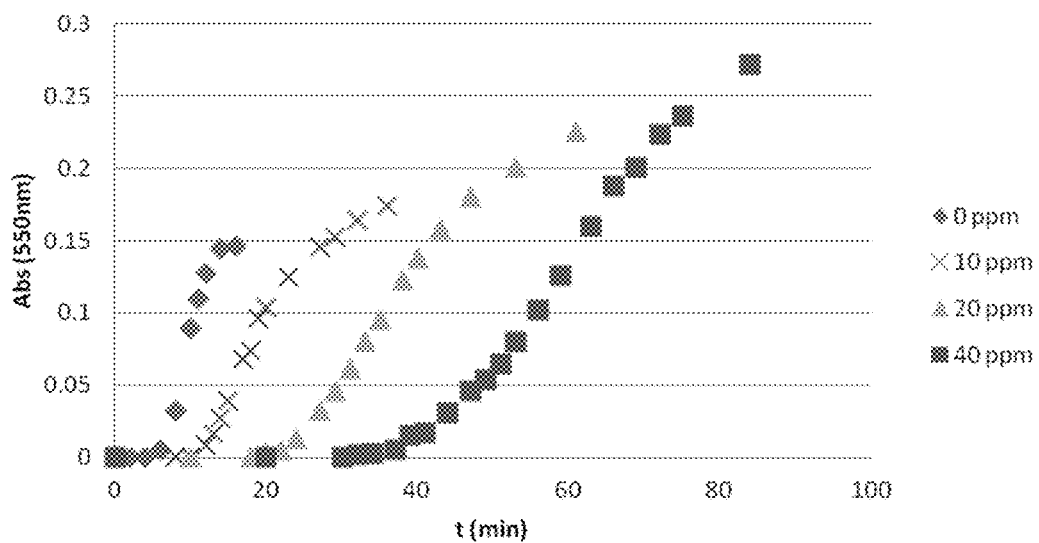
FIG. 1. Kinetics curves for the crystallisation of uric acid (400 mg/l) in synthetic urine at pH=4.67, at different theobromine concentrations. The absorbance (at 550 nm) is plotted against time (in minutes).

A turbidimeter was used to obtain the kinetic curves for uric acid crystallisation corresponding to a solution of 400 mg/l uric acid in synthetic urine (average composition similar to urine) at different pH and theobromine concentrations. FIG. 1 shows the kinetic curves for uric acid (without theobromine) at pH=4.67 and for the same uric acid concentration with 10 mg/l, 20 mg/l and 40 mg/l theobromine added. As can be seen, the induction time (time when crystals begin to appear) increases considerably with increased theobromine concentration, indicating that this substance acts as a uric acid nucleation inhibitor.

Figure 2:
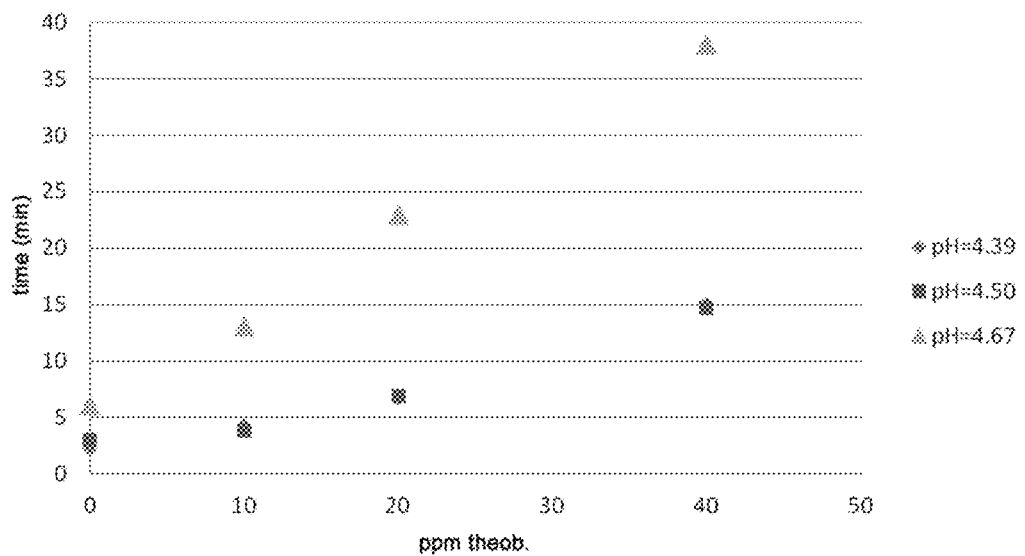
FIG. 2. Graphical representation of the induction periods (in minutes) for a solution of 400 mg/l uric acid in synthetic urine, for different pH values and concentrations of theobromine.

The induction times were therefore calculated for 400 mg/l of uric acid in synthetic urine for different pHs and different theobromine concentrations (Table 2). As can be seen in the graphs in FIG. 2, the induction times increase with increased theobromine concentrations. In addition, the inhibitory effect is much more pronounced with increased urinary pH.

TABLE 1

Induction times (and standard deviation (SD)) for a solution of 400 mg/l uric acid in synthetic urine at different pH and theobromine concentrations.

|  | Theobromine conc. (mg/l) | Induction time (min) | SD |
|---|---|---|---|
| pH = 4.39 | 0 | 2.3 | 0.07 |
|  | 10 | 4.3 | 0.4 |
|  | 20 | 6.8 | 0 |
|  | 40 | 15 | 2.8 |
| pH = 4.50 | 0 | 3 | 0 |
|  | 10 | 3.9 | 0.5 |
|  | 20 | 6.9 | 0.14 |
|  | 40 | 14.8 | 1 |
| pH = 4.67 | 0 | 6 | 0.6 |
|  | 10 | 13 | 3 |

TABLE 1-continued

Induction times (and standard deviation (SD)) for a solution of 400 mg/l uric acid in synthetic urine at different pH and theobromine concentrations.

| Theobromine conc. (mg/l) | Induction time (min) | SD |
|---|---|---|
| 20 | 23 | 3 |
| 40 | 38 | 4 |

Figure 3:
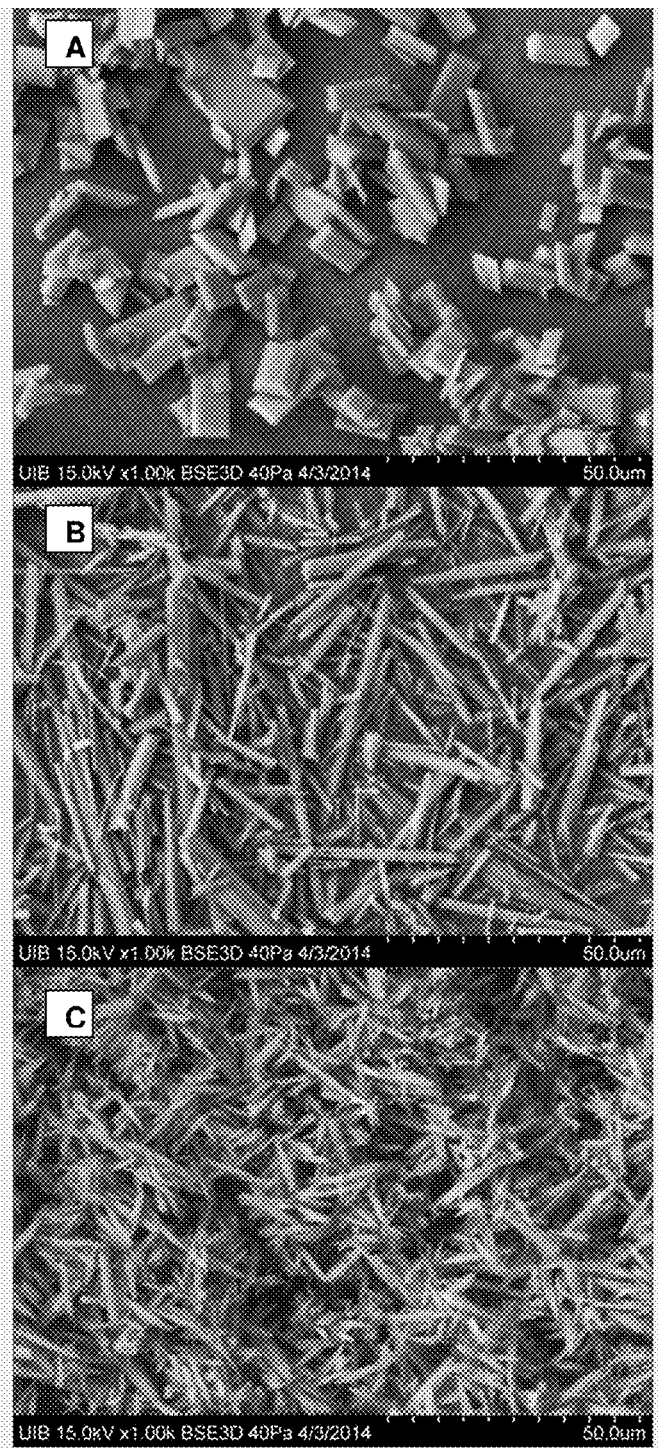
FIG. 3. Uric acid crystals observed using scanning electron microscopy, obtained in synthetic urine at pH=4.67 in the absence of theobromine (A) and the presence of 20 mg/l (B) and 40 mg/l (C) theobromine.

The precipitate generated during the turbidimetry experiment was vacuum filtered, the crystals were allowed to dry and they were then examined under a scanning electron microscope to see if there were any morphological differences between the crystals formed under differing theobromine concentrations. FIG. 3 shows the crystals generated in a 400 mg/l solution in synthetic urine at pH=4.67, without theobromine and with 20 mg/l and 40 mg/l theobromine. As can be seen, the uric acid crystals' morphology becomes much narrower and more elongated with increasing theobromine concentrations. This indicates that the inhibitor acts on the crystals' lateral faces, preventing growth in that area. Therefore, in addition to being an inhibitor of uric acid nucleation, it also acts as an inhibitor of crystal growth.

Figure 4:
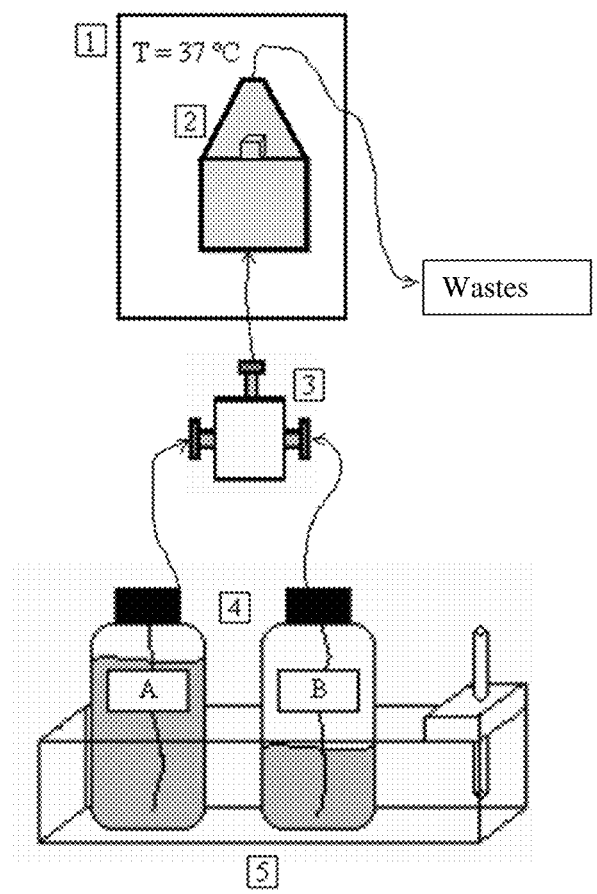
FIG. 4. Flow diagram of the system used, consisting of a synthetic urine solution and a uric acid solution, each driven by a peristaltic pump with a different flow rate, a T-shaped connection and a chamber containing the uric acid calculus.

The last experiment performed was a study on the effect of theobromine as an inhibitor of uric acid crystal growth. In order to do this, fragments of uric acid calculi from the same patient (obtained by extracorporeal shock wave lithotripsy) were placed in a flow of synthetic urine with 400 mg/l uric acid and different concentrations of theobromine using a flow system as shown in FIG. 4. This system had two peristaltic pumps. One of them pumped the synthetic urine without uric acid, at pH=3.00 (4-A). The other pumped a 2 g/l solution of uric acid at pH=10.70 (4-B). The temperature of both solutions was regulated at 37° C. (5). For the phases studying the effects of theobromine, it was dissolved in the synthetic urine solution. These solutions (synthetic urine and uric acid) were mixed in the T-shaped connection (3) to produce synthetic urine with 400 mg/l uric acid at a pH or around 5.40. The peristaltic pumps had different flow rates as the final synthetic urine had to have 400 mg/l uric acid and the total daily volume had to be 750 ml, which is the mean volume of urine that passes through a kidney.

The solution resulting from the mixing of the uric acid and synthetic urine solutions is passed through a chamber containing a uric acid calculus of known weight (2); the chamber was located within an oven at 37° C. (1). The flow system is maintained for 48 hours. At the end of this time the calculi are dried in an oven and weighed again. The % increase in mass is then calculated.

Figure 5:
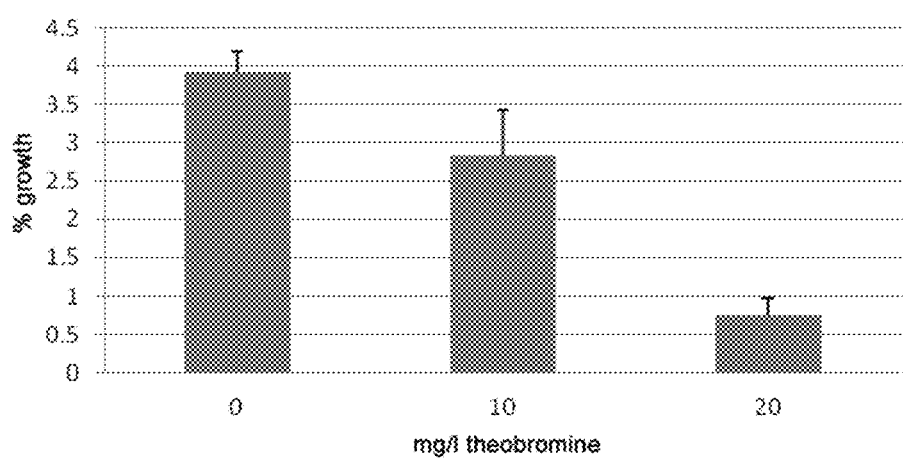
FIG. 5. Percentage increase in mass (with standard deviation bar) in vitro of renal uric acid calculi fragments from a single patient, obtained after extracorporeal shock wave lithotripsy, when subjected to a constant flow of synthetic urine for 48 hours in the presence of different concentrations of theobromine.

FIG. 5. shows the percentage increase in mass in relation to the concentration of theobromine. A total of 5 calculi were used for each theobromine concentration. As can be seen, as the theobromine concentration increases, the % in mass of the calculus fragments decreases, with the increase in mass practically zero at 20 mg/l theobromine.

Figure 6:
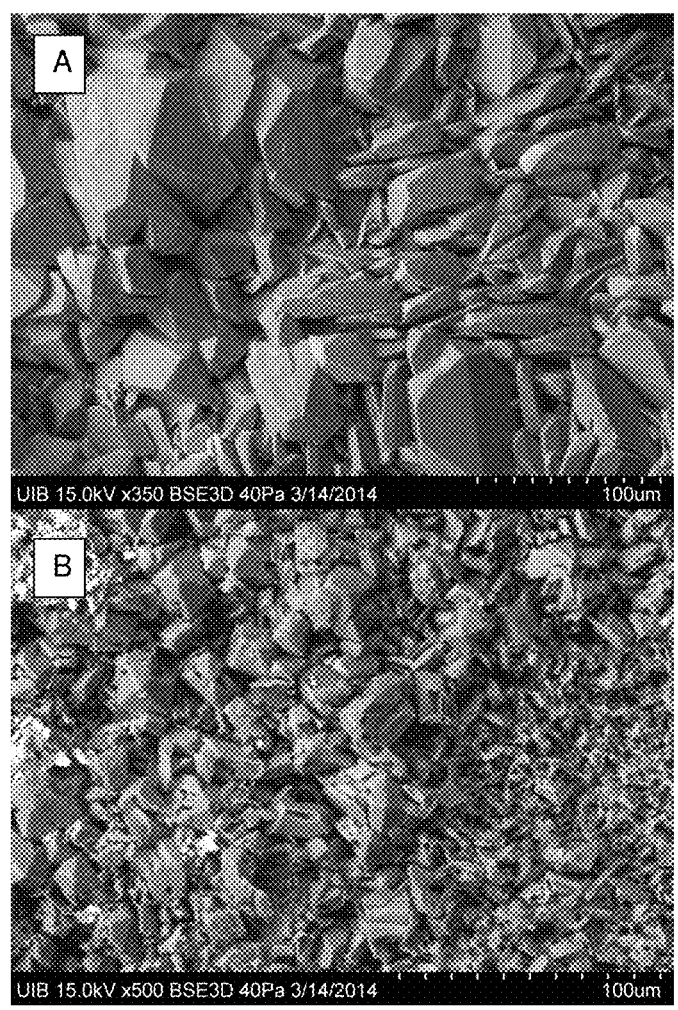
FIG. 6. Scanning electron microscope image of fragments of renal uric acid calculi that have grown in contact with synthetic urine without theobromine (A) and with 20 mg/l theobromine (B).

A total of two fragments were examined using scanning electron microscopy in order to see if there were any morphological differences between the calculi in relation to theobromine concentration after the calculi were exposed to the flow process (FIG. 6). It can be seen that when there is no inhibitor the fragments that have grown on the surface of the calculi are larger than when theobromine is present.

All the previous experiments demonstrate theobromine's high capacity to inhibit uric acid crystal nucleation and growth, with a potential application in the treatment and prevention of renal lithiasis.

The invention claimed is:

1. A method of treating renal lithiasis in a subject, comprising administering to the subject a composition comprising a compound with general formula (I)

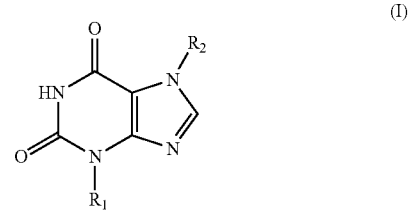

where: $R_1$ and $R_2$ are methyl, or any of the compound's pharmaceutically acceptable salts, wherein the renal lithiasis is uric acid renal lithiasis.

2. The method of claim 1, for reducing risks and improving health status of the subject with diseases related to the crystallisation of uric acid.

3. The method of claim 1, where the composition is a pharmaceutical composition, functional food, nutraceutical product or food supplement.

4. The method of claim 1, where the compound of general formula (I) wherein R1 and R2 are methyl, or any of the compounds pharmaceutically acceptable salts, is administered in a dose of between 100 mg/day and 380 mg/day.

5. The method of claim 1, where the composition further comprises lactose, sucrose, talc, magnesium stearate, cellulose, calcium salts, gelatine and/or fatty acids.

* * * * *